(12) United States Patent
Liu et al.

(10) Patent No.: US 8,962,037 B2
(45) Date of Patent: Feb. 24, 2015

(54) DICALCIUM PHOSPHATE CERAMICS, DICALCIUM PHOSPHATE/HYDROXYAPATITE BIPHASIC CERAMICS AND METHOD OF MANUFACTURING THE SAME

(75) Inventors: Sung-Tsuen Liu, Miaoli County (TW); Sung-Ching Chen, New Taipei (TW); Hui-Chun Lai, New Taipei (TW); Wan-Ting Huang, New Taipei (TW)

(73) Assignee: Maxigen Biotech Inc., New Taipei (TW)

( * ) Notice: Subject to any disclaimer, the term of this patent is extended or adjusted under 35 U.S.C. 154(b) by 534 days.

(21) Appl. No.: 13/023,318

(22) Filed: Feb. 8, 2011

(65) Prior Publication Data

US 2012/0201870 A1    Aug. 9, 2012

(51) Int. Cl.

| | | |
|---|---|---|
| *A01N 59/24* | (2006.01) | |
| *A61K 6/083* | (2006.01) | |
| *C01B 15/16* | (2006.01) | |
| *C04B 35/447* | (2006.01) | |
| *A61L 27/12* | (2006.01) | |
| *A61L 27/56* | (2006.01) | |
| *C01B 25/32* | (2006.01) | |
| *C04B 38/04* | (2006.01) | |
| *C04B 111/00* | (2006.01) | |

(52) U.S. Cl.
CPC ............... *C04B 35/447* (2013.01); *A61L 27/12* (2013.01); *A61L 27/56* (2013.01); *C01B 25/32* (2013.01); *C04B 38/04* (2013.01); *C04B 2235/3212* (2013.01); *C04B 2235/5427* (2013.01); *C04B 2235/606* (2013.01); *A61L 2430/02* (2013.01); *A61L 2430/12* (2013.01); *C04B 2111/00836* (2013.01)
USPC ............ 424/602; 424/426; 423/307; 523/105

(58) Field of Classification Search
CPC .................... A61L 27/12; A61K 33/42; A61F 2310/00293
See application file for complete search history.

(56) References Cited

U.S. PATENT DOCUMENTS

| | | | |
|---|---|---|---|
| 7,381,262 B2 * | 6/2008 | Tas ................................ | 106/690 |
| 2002/0114938 A1 * | 8/2002 | Matsumoto ................ | 428/307.3 |
| 2006/0292350 A1 * | 12/2006 | Kawamura et al. ........... | 428/189 |

\* cited by examiner

*Primary Examiner* — Michael G Hartley
*Assistant Examiner* — Lance Rider
(74) *Attorney, Agent, or Firm* — WPAT, P.C.; Anthony King; Kay Yang

(57) ABSTRACT

The present invention discloses a method of manufacturing pure dicalcium phosphate ceramics or dicalcium phosphate/hydroxyapaite (HA) biphasic ceramics for medical applications in hard tissue areas to be used as implant materials. These ceramic implant materials are in granular form or in block form, and are prepared by using an acidic phosphate compound, a basic calcium phosphate compound comprising HA, and water. The dicalcium phosphate ceramic comprises either dicalcium phosphate dihydrate ($CaHPO_4 \cdot 2H_2O$, DCPD) or dicalcium anhydrous ($CaHPO_4$, DCPA). Wherein, when the acidic phosphate compound is provided in an amount stoichiometrically equal to or in excess relative to the basic calcium phosphate compound, a reaction product is the DCPD or DCPA ceramic; when the acidic phosphate compound is provided in the amount stoichiometrically less than the basic calcium phosphate compound, the reaction product is the DCPD/HA or DCPA/HA biphasic ceramic.

12 Claims, 4 Drawing Sheets

DICALCIUM PHOSPHATE CERAMICS, DICALCIUM PHOSPHATE/HYDROXYAPATITE BIPHASIC CERAMICS AND METHOD OF MANUFACTURING THE SAME

BACKGROUND OF THE INVENTION

1. Field of the Invention

The present invention relates to a manufacturing method of new bioresorbable calcium phosphate ceramics, and more particularly to a method of manufacturing dicalcium phosphate ceramics and dicalcium phosphate/hydroxyapatite (HA) biphasic ceramics useful as bone graft materials, bone substitutes and bone fillers.

2. Description of Related Art

The major inorganic constitute of hard tissue is biological apatite. For example, bone has 65% to near 70% of biological apatite, and teeth contain more than 98% biological apatite. Hydroxyapatite (HA) is a calcium phosphate compound which has similar crystal structure as biological apatite. In principle, HA should be an ideal candidate as hard tissue replacement material. However, the precipitated HA particles are very fine powder. Because of manipulation requirement, this hinders the use of precipitated HA as useful hard tissue replacement material. Similar problems exist for other precipitated calcium phosphate particles, such as dicalcium phosphate for medical use.

In the early 1980, attempts were made to prepare calcium phosphate ceramics in the granular form or block form by ceramic sintering technique. In the last thirty year or so, many types of calcium phosphate ceramics have been prepared. Among these HA, α- and β-tricalcium phosphate (TCP) ceramics have been extensively studies. Clinical studies confirmed that most of the calcium phosphate ceramics with Ca/P mole ratio equal to one or higher, such as dicalcium phosphate, HA, TCP and tetracalcium phosphate (TTCP), have excellent compatibility and are well accepted by the hard tissue and soft tissue. Experiment results indicated that dense HA is non-resorbable while other porous calcium phosphate ceramics are resorbable. In general, β-TCP ceramic resorbs faster than HA but has weaker mechanical strength than HA. To obtain ceramics combining good mechanical properties with bioresorption, a biphasic calcium phosphate (BCP) ceramic has been prepared. These biphasic ceramics are a mixture of HA and β-TCP. Most of the above ceramics is either resorbed too slowly or difficult to control the bioresorption rate.

Brown and Chow in 1986 were the first to present calcium phosphate in the cement form for medical applications. The main constitute of the cement is TTCP and dicalcium phosphate, and the main reaction product is HA. After that, calcium phosphate cements with different formulations have been developed. Main advantages of calcium phosphate cement are moldable. Calcium phosphate cements developed can be classified according to their reaction products. Basically, there are two major types of calcium phosphate cements namely the HA cement and dicalcium phosphate dihydrate (DCPD) cement. Similar to high temperature HA, HA cement is resorbed very slowly. Major constitutes of DCPD are basic calcium phosphate, such as α- or β-TCP or HA, with acidic phosphate compounds, such as phosphoric acid or monocalcium phosphate, together with some setting solution. In general, this type of cement is quite acidic. Beside the reaction product is DCPD, it also contains considerable amount of unreacted constitute. The physical and chemical properties of this type of cement also vary considerable. For example, using β-TCP to prepare DCPD cement, it is always keep basic calcium phosphate in much excess. Beside, it always keeps some crystal growth inhibitor to control the setting time. After setting, beside the formed DCPD, it also contains the excess unreacted product and some setting regulating reagent. On the other hand, if stoichiometric amount are used, the setting cement is too acidic for use. If HA is used instead of TCP, the setting time is difficult to control and the setting cement is too acidic. Similar to precipitated HA, dicalcium phosphate prepared from precipitated method is also a fine powder and have manipulation problem. Even the powder can be very pure; it can not be used for bone filler or bone substitute because of manipulation problem.

In recent year, calcium sulfate also has been used as bone filler or replacement material. However, the major drawbacks are the rapid bioresorption and low strength. This makes it less useful in larger defects and when fracture healing exceeds 4-6 weeks. From practical point of view, bioceramics for bone filler or as bone substitute materials should have both controllable physical and chemical properties, such as mechanical strength and bioresorption rate.

There are many types of calcium phosphate compounds. Among these are dicalcium phosphate, calcium pyrophosphate, α-TCP, β-TCP, HA and TTCP. Some of these compounds can be prepared only by high temperature technique, such as TTCP and α-TCP. Some of them can only form from precipitation method. Among these are DCPD and DCPA. Other calcium phosphate minerals, such as HA, apatite minerals, and calcium pyrophosphate, can be prepared by either high temperature sintering technique or the precipitation method. For medical applications, such as bone substitute or bone filler, most of the calcium phosphate ceramics are prepared as granular form or block form by high temperature sintering technique. For example, commercial calcium phosphate ceramics for medical applications are block form or granular form of HA, β-TCP and biphasic calcium phosphate which contains both HA and β-TCP. Precipitated calcium phosphate compounds are always very fine powder. Because of manipulation difficulties, precipitated calcium phosphate materials have limited applications as bone substitute or bone filler. Pure DCPD are normally prepared by precipitation method. DCPA can be obtained by precipitation method or by dehydrating DCPD at high temperature. Dicalcium phosphates prepared by this method are also very fine powder. They have difficulties to be used in the area of bone graft or bone filler. Granular form of dicalcium phosphate can be prepared from granulation technique. However, it always contains binder in the preparation process. Besides, granule preparation from granulation technique is not strong. These cause the precipitated dicalcium phosphate having difficulties for using in the hard tissue area.

Moreover, it is well known that DCPD can be precipitated from calcium phosphate saturated solution at pH value near 4 or lower. However, when the pH of calcium phosphate saturated solution is near 7 or higher, the precipitated calcium phosphate is HA or apatite minerals.

Therefore, most of the above cements or ceramics have certain disadvantages. The present invention is aimed to prepare pure dicalcium phosphate (either dihydrate or anhydrous) and its composite mixture with HA for medical applications especially in the bone substitute or bone filler area to overcome the above disadvantages.

SUMMARY OF THE INVENTION

Accordingly, an object of the present invention is to provide a manufacturing method of dicalcium phosphate ceramics and dicalcium phosphate/hydroxyapatite (HA) biphasic ceramics having excellent biocompatibility and controllable bioresorption rates and being useful in orthopedic and maxillofacial surgeries and dental applications.

According to the object of the present invention, it is provided with a method of manufacturing dicalcium phosphate dihydrate (DCPD) ceramic, dicalcium phosphate anhydrous (DCPA) ceramic, DCPD/HA biphasic ceramic, or DCPA/HA biphasic ceramic, comprising the following steps: forming a mixture containing an acidic phosphate compound with a basic calcium phosphate compound comprising HA; adding water to the mixture to form paste; and shaping the paste to a desired shape and hardening the paste to obtain a solid material; washing and leaching the solid material until a surface pH of the solid material reaches about 4.5 or higher; and drying the solid material at room temperature or below 95° C. to obtain DCPD ceramic or DCPD/HA biphasic ceramic, or drying the solid material at 100° C. or higher to obtain DCPA ceramic or DCPA/HA biphasic ceramic. Wherein, when the acidic phosphate compound is provided in an amount stoichiometrically equal to or in excess relative to the basic calcium phosphate compound, a reaction product is the DCPD ceramic or the DCPA ceramic; when the acidic phosphate compound is provided in the amount stoichiometrically less than the basic calcium phosphate compound, the reaction product is the DCPD/HA biphasic ceramic or the DCPA/HA biphasic ceramic.

Preferably, besides comprising HA, the basic calcium phosphate compound further comprises tricalcium phosphate, calcium carbonate, calcium oxide, calcium hydroxide, or a combination thereof.

Preferably, the acidic phosphate compound comprises monocalcium phosphate monohydrate, monocalcium phosphate anhydrous, phosphoric acid, or a combination thereof.

Preferably, the DCPD ceramic, DCPA ceramic, DCPD/HA biphasic ceramic, or DCPA/HA biphasic ceramic is in granular form or in block form.

Preferably, the DCPD/HA biphasic ceramic or DCPA/HA biphasic ceramic comprises dicalcium phosphate minerals from about 30% to about 95% by weight and HA from about 5% to about 70% by weight.

Furthermore, the present invention further provides a bioceramic for medical applications in hard tissue areas, being selected from the group consisting of the DCPD ceramic, DCPA ceramic, DCPD/HA biphasic ceramic, and DCPA/HA biphasic ceramic, which are manufactured according to the above-mentioned method.

Preferably, the DCPD ceramic, DCPA ceramic, DCPD/HA biphasic ceramic, or DCPA/HA biphasic ceramic is in block form with a macroporous structure.

Briefly, the dicalcium phosphate ceramics, dicalcium phosphate/HA biphasic ceramics and the manufacturing method thereof according to the present invention can provide one or more advantages as follows:

(1) A person skilled in the art knows that the higher the solubility, the larger the Ksp value. At 25° C., the Ksp value of DCPA is $1\times10^{-6.90}$; the Ksp value of DCPD is $1\times10^{-6.59}$; the Ksp value of α-tricalcium phosphate (α-TCP) is $1\times10^{-25.5}$; the Ksp value of β-tricalcium phosphate β-TCP) is $1\times10^{-28.9}$; and the Ksp value of HA is $1\times10^{-116.8}$ (Dent Mater J 2009; 28(1): 1-10). Moreover, the Ksp value of calcium sulfate is $9.1\times10^{-6}$ at 25° C. Therefore, the dicalcium phosphate ceramics, both DCPD ($CaHPO_4.2H_2O$) and DCPA ($CaHPO_4$) ceramics, in accordance with the present invention have solubilities which are lower than calcium sulfate but higher than tricalcium phosphates (TCPs) and HA. That is, it is expected that the dicalcium phosphate ceramics and their combination with HA will provide excellent biocompatibility with the bioresorption rate longer than calcium sulfate but faster than HA and TCPs.

(2) The dicalcium phosphate/HA biphasic ceramics, both DCPD/HA biphasic ceramic and DCPA/HA biphasic ceramic, of the present invention can have different ratios of the dicalcium phosphate minerals (i.e. DCPD and DCPA) and HA according to desired bioresorption rates. Besides, the dicalcium phosphate ceramics and dicalcium phosphate/HA biphasic ceramics can be manufactured in granular or block form, selectively with a macroporous structure, by using different reagents. Accordingly, the present invention provides the new bioresorbable calcium phosphate ceramics with controllable bioresorption rates by adjusting the ratios of the dicalcium phosphate minerals and HA, kinds of reactants, types of solid forms, or porous amounts and sizes. That is, the present invention can control the bioresorption rates of the dicalcium phosphate ceramics and dicalcium phosphate/HA biphasic ceramics depending on portions and areas of hard tissue to be repaired.

(3) The dicalcium phosphate ceramics and dicalcium phosphate/HA biphasic ceramics in accordance with the present invention has a near-neutral pH (about 4.5 or higher, preferably 5 to 6.5), and thus after implantation, these ceramics will not cause side effects, such as irritation and inflammatory reactions.

Other aspects of the present invention will be illustrated partially in the subsequent detailed descriptions, conveniently considered partially through the teachings thereof, or comprehended by means of the disclosed embodiments of the present invention. Various aspects of the present invention can be understood and accomplished by using the components and combinations specifically pointed out in the following claims. It is noted that the aforementioned summary and the following detailed descriptions of the present invention are exemplary and illustrative, rather than being used to limit the scope of the present invention thereto.

BRIEF DESCRIPTION OF THE DRAWINGS

The exemplary embodiments of the present invention will be understood more fully from the detailed description given below and from the accompanying drawings of various embodiments of the invention.

DETAILED DESCRIPTION OF THE PREFERRED EMBODIMENTS

Figure 1:
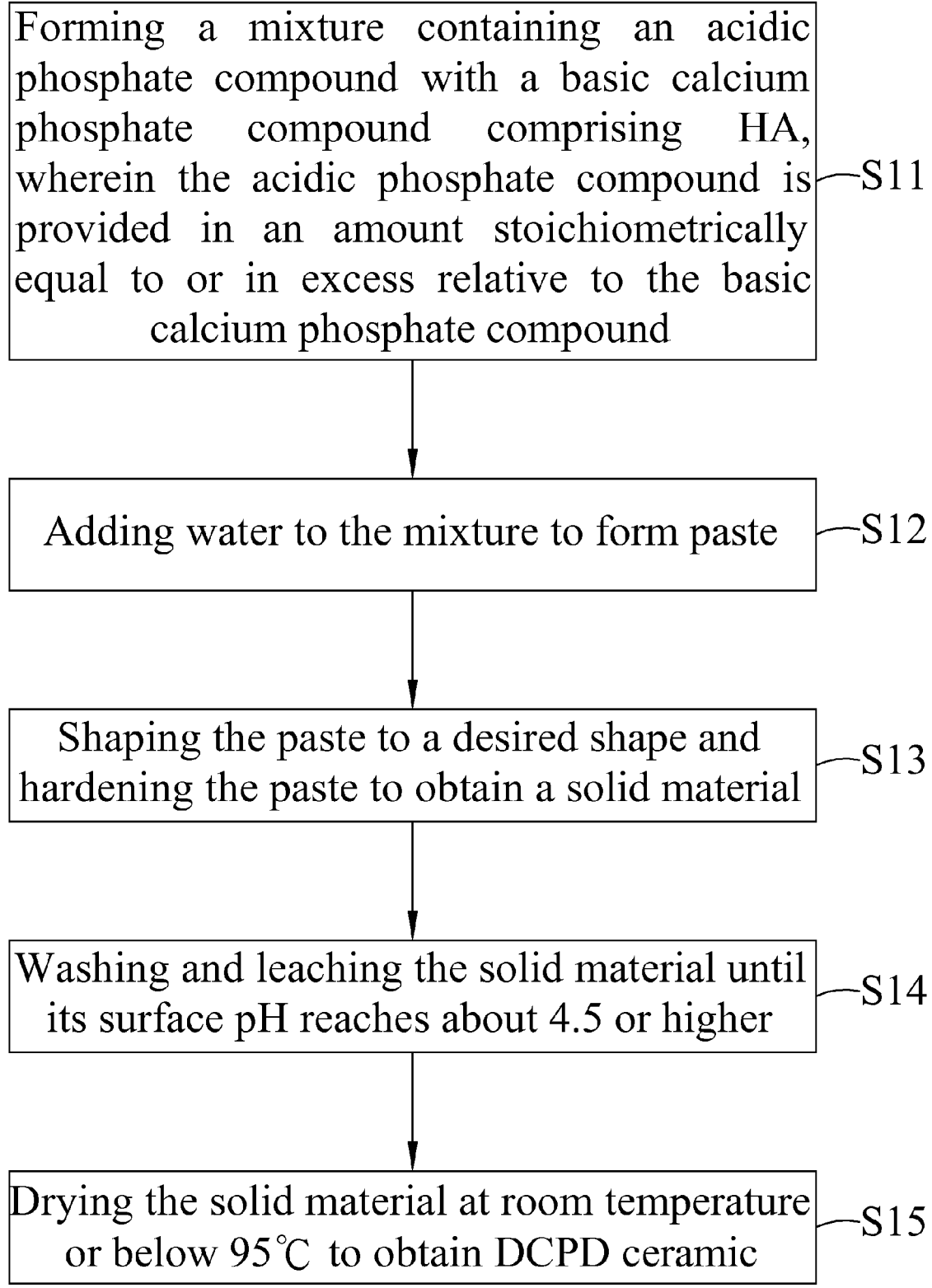
FIG. 1 illustrates a flow chart of a method of manufacturing DCPD ceramic in accordance with a first embodiment of the present invention.

Referring to FIG. 1, which is a flow chart of a method of manufacturing dicalcium phosphate dihydrate ($CaHPO_4.2H_2O$, DCPD) ceramic in accordance with a first embodiment of the present invention. The method comprises the following steps. In step S11, a mixture containing an acidic phosphate compound with a basic calcium phosphate compound comprising HA is formed, wherein the acidic phosphate compound is provided in an amount stoichiometrically equal to or in excess relative to the basic calcium phosphate compound. In step S12, water is added to the mixture to form paste. In step S13, the paste is molded or shaped into a desired shape and hardened to obtain a solid material. In step S14, the solid material is washed and leached until its surface pH reaches about 4.5 or higher, preferably 5 to 6.5. In step S15, the solid material is dried at room temperature or below 95° C. to obtain the DCPD ceramic.

Figure 2:
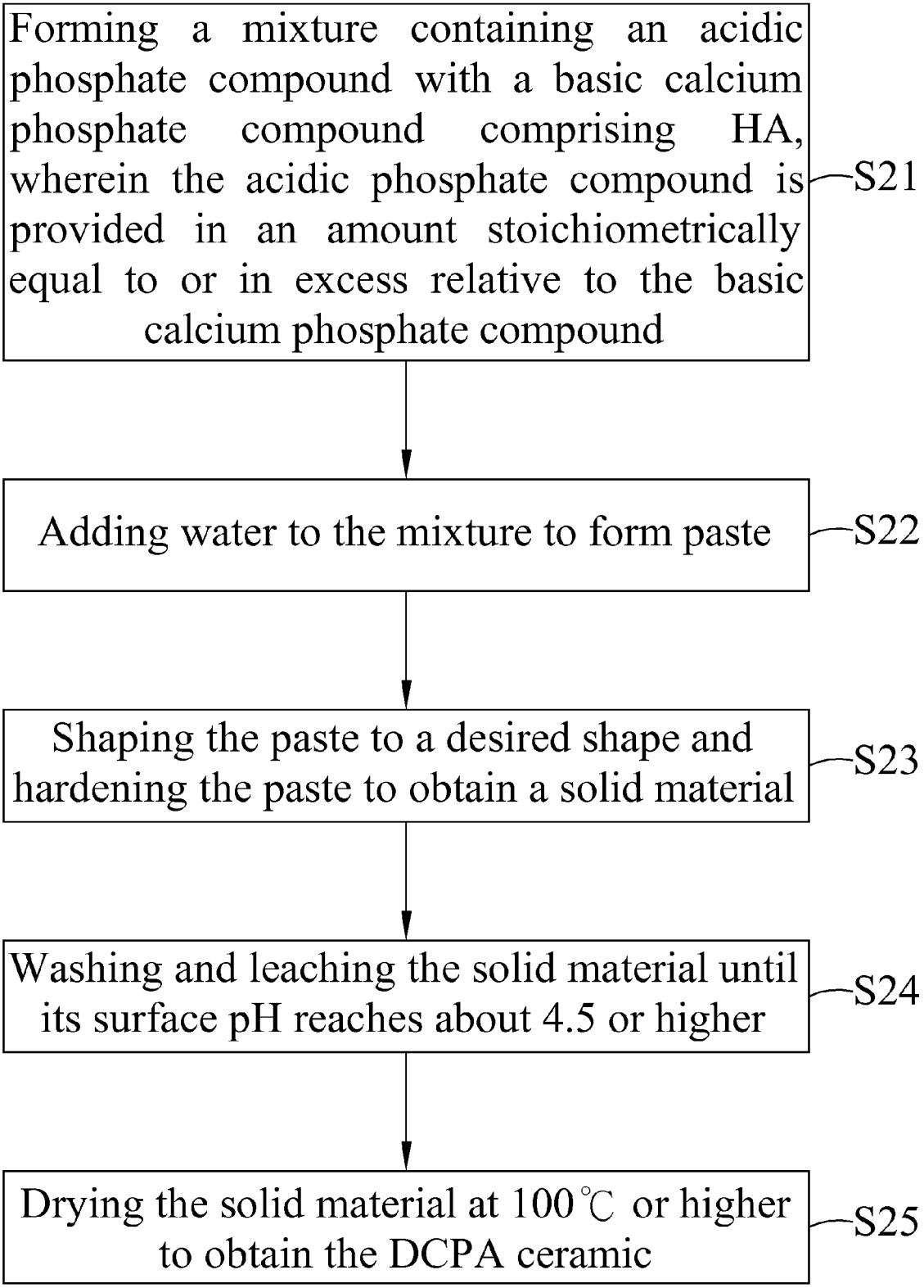
FIG. 2 illustrates a flow chart of a method of manufacturing DCPA ceramic in accordance with a second embodiment of the present invention.

Referring to FIG. 2, which is a flow chart of a method of manufacturing dicalcium phosphate anhydrous ($CaHPO_4$, DCPA) ceramic in accordance with a second embodiment of the present invention. The method comprises the steps as follows. In step S21, a mixture containing an acidic phosphate compound with a basic calcium phosphate compound comprising HA is obtained, wherein the acidic phosphate compound is provided in an amount stoichiometrically equal to or in excess relative to the basic calcium phosphate compound. In step S22, water is added to the mixture to form paste. In step S23, the paste is molded or shaped into a desired shape and hardened to obtain a solid material. In step S24, the solid material is washed and leached until its surface pH reaches about 4.5 or higher, preferably 5 to 6.5. In step S25, the solid material is dried at 100° C. or higher to obtain the DCPA ceramic.

Figure 3:
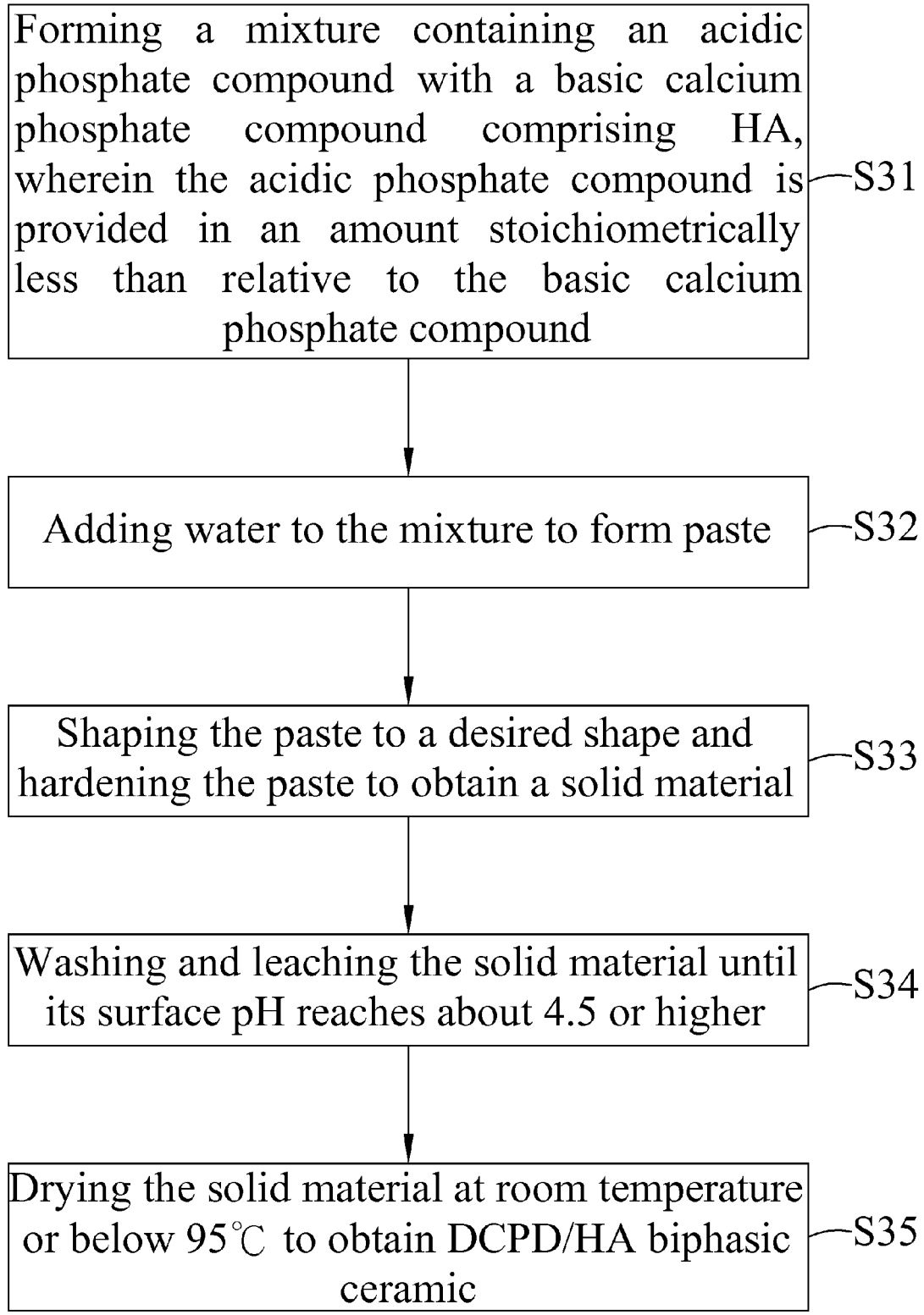
FIG. 3 illustrates a flow chart of a method of manufacturing DCPD/HA biphasic ceramic in accordance with a third embodiment of the present invention.

Referring to FIG. 3, which is a flow chart of a method of manufacturing DCPD/hydroxyapatite (HA) biphasic ceramic in accordance with a third embodiment of the present invention. The method comprises the following steps. In step S31, a mixture containing an acidic phosphate compound with a basic calcium phosphate compound comprising HA is formed, wherein the acidic phosphate compound is provided in an amount stoichiometrically less than the basic calcium phosphate compound. In step S32, water is added to the mixture to form paste. In step S33, the paste is molded or shaped into a desired shape and hardened to obtain a solid material. In step S34, the solid material is washed and leached until its surface pH reaches about 4.5 or higher, preferably 5 to 6.5. In step S35, the solid material is dried at room temperature or below 95° C. to obtain the DCPD/HA biphasic ceramic.

Figure 4:
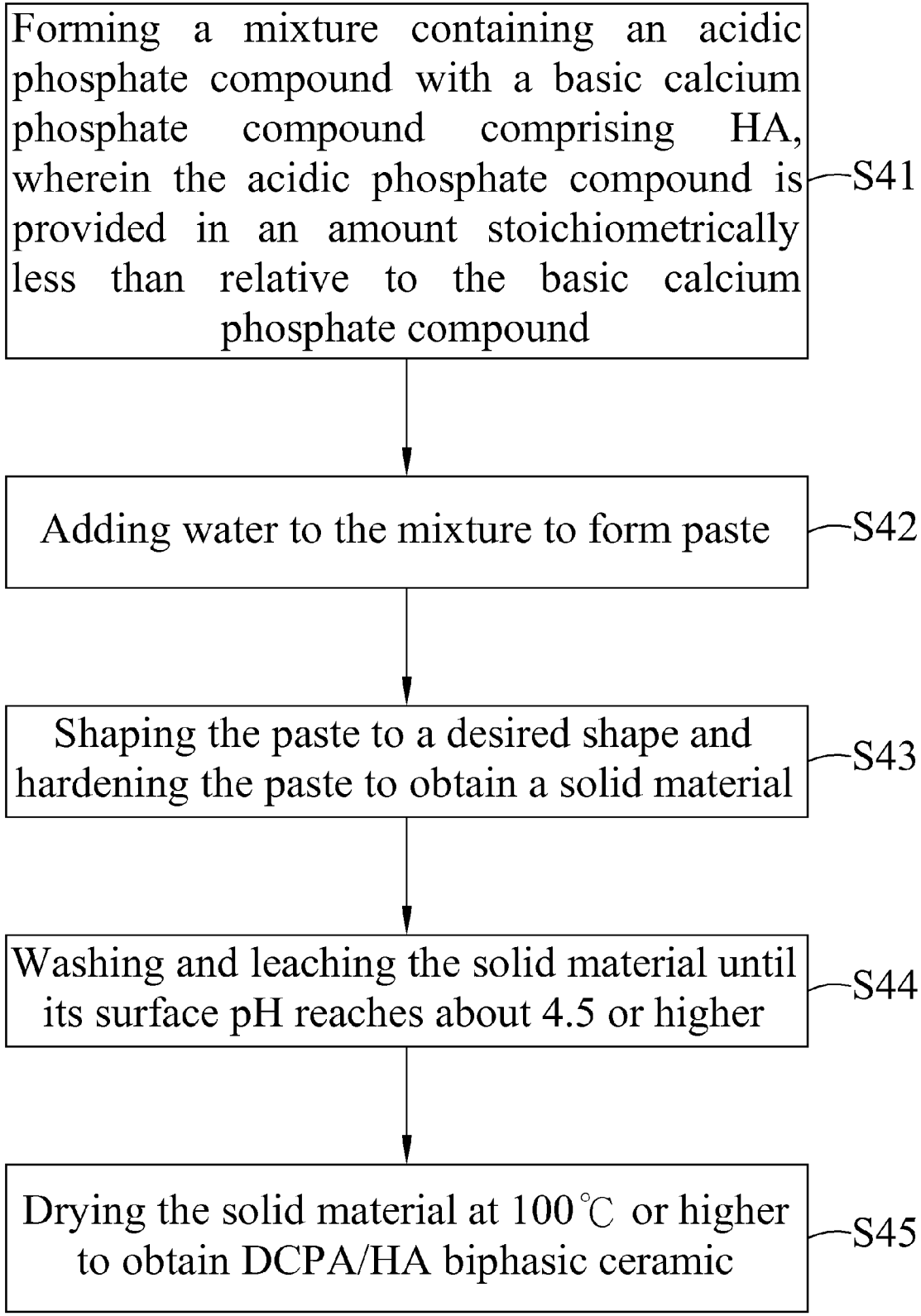
FIG. 4 illustrates a flow chart of a method of manufacturing DCPA/HA biphasic ceramic in accordance with a fourth embodiment of the present invention.

Referring to FIG. 4, which is a flow chart of a method of manufacturing DCPA/HA biphasic ceramic in accordance with a fourth embodiment of the present invention. The method comprises the steps as follows. In step S41, a mixture containing an acidic phosphate compound with a basic calcium phosphate compound comprising HA is obtained, wherein the acidic phosphate compound is provided in an amount stoichiometrically less than the basic calcium phosphate compound. In step S42, water is added to the mixture to form paste. In step S43, the paste is molded or shaped into a desired shape and hardened to obtain a solid material. In step S44, the solid material is washed and leached until its surface pH reaches about 4.5 or higher, preferably 5 to 6.5. In step S45, the solid material is dried at 100° C. or higher to obtain the DCPA/HA biphasic ceramic.

According to the above-mentioned descriptions in embodiments, after the step S13, S23, S33, or S43, the solid material may be dried at room temperature to about 90° C. The basic calcium phosphate compound may have a Ca/P molar ratio of more than 1, and the acidic phosphate compound may have a Ca/P molar ratio of less than 1. Alternatively, besides comprising HA, the basic calcium phosphate compound may further comprise tricalcium phosphate (TCP), calcium carbonate, calcium oxide, calcium hydroxide, or a combination thereof. The acidic phosphate compound may comprise monocalcium phosphate monohydrate ($Ca(H_2PO_4)_2 \cdot H_2O$, MCPM), monocalcium phosphate anhydrous ($Ca(H_2PO_4)_2$, MCPA), phosphoric acid, or a combination thereof.

In addition, the acidic phosphate compound may be provided in the amount stoichiometrically in excess of about 0.1% to about 20% by weight for obtaining the DCPD ceramic or the DCPA ceramic. The DCPD ceramic or the DCPA ceramic may be at least 97% in purity. HA used may be sintered HA or precipitated HA. HA used may be fine powder or in granular form with a particle size in a range of about 0.1 mm to about 2 mm. Furthermore, the DCPD ceramic, DCPA ceramic, DCPD/HA biphasic ceramic, or DCPA/HA biphasic ceramic may be in granular form, preferably with a particle size in a range of about 0.1 mm to about 5 mm, or in block form, preferably with a macroporous structure. The DCPD/HA biphasic ceramic or DCPA/HA biphasic ceramic may comprise dicalcium phosphate minerals from about 30% to about 95% by weight and HA from about 5% to about 70% by weight.

In another embodiment, the formed mixture further comprises porogen, such as sodium chloride, potassium chloride, maltose, sucrose, or a combination thereof.

In other embodiments, the DCPD ceramic, DCPA ceramic, DCPD/HA biphasic ceramic, or DCPA/HA biphasic ceramic are provided according to the above-mentioned methods and contents.

The present invention provides low temperature calcium phosphate ceramics in granular form or block form which contain near pure dicalcium phosphate or combination of dicalcium phosphate with HA. These ceramics are useful as bone graft or bone filler material. The dicalcium phosphate can be either DCPD or DCPA. The ceramics in granular form may have irregular shapes with size of about 0.1 mm to about 5 mm. The block form can be a pellet type or any shape. The block form can also be prepared with a macroporous structure. The present ceramic is a useful bone filler or bone replacement material which has the bioresorption rate slower than Plaster of Paris but faster than HA or TCPs.

The present invention may use HA and monocalcium phosphate or phosphoric acid as the reaction component for preparing the dicalcium phosphate ceramics or dicalcium phosphate/HA biphasic ceramics. The Ca/P mole ratio in the initial material is below 1 or near 1 to get pure dicalcium phosphate ceramics. For dicalcium phosphate/HA biphasic ceramics, the Ca/P mole ratio is higher than 1. However, it does not include any setting regulating agent. Setting time is not a major concern in the current preparation. After setting, the block form or pellet is soaked in pure water several times until the final soaking water shows a pH values near 5 or near neutral. If the macroporous structure is needed, the setting powder may include water-leachable organic solids or inorganic solids, such as sugar, sodium chloride or maltose. After setting, the soluble material is then leached out to create the macroporous structure. To produce granular materials, the setting solid material is crashed and sieved to collect the granules with desired particle size. Similar to the block form, the granules were soaked in pure water several times until the final soaking water shows a pH value near 6 or near neutral. The above ceramics are then air dry or heated dry below 100° C. to obtain the DCPD ceramics or DCPD/HA biphasic ceramics. For the DCPA ceramics, the above ceramics is dehydrated at temperature near 100° C. or above for enough time to ensure the conversion of DCPD to DCPA. These ceramics give flexibility in controlling the bioresorption rate for medical use and provide reasonable good mechanical strength.

In the preparation of pure DCPD, the basic calcium phosphate compound to be used can be either TCP or HA. However, HA will be preferable because of slow setting time and easy to control. For the acidic phosphate compound, monocalcium phosphate (either anhydrous of monohydrate) or phosphoric acid can be used. Unlike the ordinary calcium phosphate cement preparation, the acidic phosphate compound will keep at least in equal mole ratio, preferably with acidic phosphate compound in excess. In this circumstance, there will have enough or more than enough of acidic phosphate compound to cause the complete reaction of the basic calcium phosphate compound. After the acidic phosphate compound and basic calcium phosphate compound are mixed, enough water is added and continued to mix until a workable paste is formed. Water to be used will keep in optimal condition in order to get a strong setting solid material. If too much water is used, the setting solid material is relatively weak. The paste will then be cast into the desired shape or molded into the desired form. Since the setting time is not critical in the pure dicalcium phosphate preparation, one can wait until the product is completely set and becomes hard. Shortly before the material become set, a needle type of tool can be used to create a macroporous structure of the setting solid material.

For example, as shown in the following reaction equation, if HA and monocalcium phosphate are used in the preparation of the DCPD ceramic, few % to near 20% excess by weight of monocalcium phosphate can be used. To get better mixing, the initial reactants are grounded first or fine powders are used. The mixed powders are then mixed with enough water to form a workable paste. Theses pastes are then cast or molded into the desired shape. After the paste becomes hard, the setting solid material is air dried or dried blow 90° C. first, and the dried solid material is then leached with pure water. Alternatively, the leaching process can be performed without the drying process. The setting solid material will be very acidic because of the excess acidic component. Since the acidic component is very soluble, the entrapped acidic component after setting can be easily leached out by soaking the setting solid material in pure water. In the leaching process, the leaching water is suggested to change occasionally. The leaching process is completed when the final leaching liquid has pH values reach near 5, preferably between 5 and 6.5. This solid shape DCPD is then air dried to get the final product. Both precipitated HA and sintered hydroxyaptite can be used. However, if a strong dicalcium phosphate is needed, sintered HA is a preferred choice, since less water is required for paste preparation. The final set solid DCPD can be any form, such as block form, cylinder form or any irregular shape.

$$Ca_5(PO_4)_3OH + 2Ca(H_2PO_4)_2 + 13H_2O \longrightarrow 7CaHPO_4 \cdot 2H_2O$$
HA             MCPA                              DCPD In the preparation of pure DCPD ceramic in granular form with a particle size in a range of about 0.1 mm and about 5 mm, the above dried solid product can be further processed by crushing and sieving to obtain the desired size of granule material. Another alternative method to obtain the granular DCPD ceramic is to crush the setting solid material before washing and drying. After crushing and sieving, the selected granules are washing and leaching followed the procedure as in the block form preparation. If pure DCPA is needed, the dried block or granule DCPD is dehydrated at 100° C. or slightly higher until dehydration is completed. The prepared pure DCPD or DCPA ceramics in block form or granular form should have very good biocompatibility and reasonable good mechanical strength to meet medical applications.

In the preparation of DCPD/HA biphasic biphasic ceramic, similar procedure is followed except excess basic calcium phosphate component, HA, is used. HA used in this preparation can be fine powder, granular form or a mixture thereof. In such case, the initial setting components are still acidic. The setting component is then leached with continuing changing of water until the leaching solution has pH value near 5, preferably 5 to 6.5. The other procedure of preparation is similar to those of pure DCPD ceramic. The final DCPD/HA biphasic ceramic prepared can have HA of about 5% to about 70% by weight and DCPD of about 95% to about 30% by weight. In the preparation of DCPA/HA biphasic ceramic, the dehydration of dihydrate to anhydrous will follow the same procedure as in the preparation of pure DCPA ceramic.

In some cases, calcium carbonate, calcium hydroxide or calcium oxide can be used to replace part of basic calcium phosphate compound used. Macroporous product can be produced by using calcium carbonate to replace part of HA. Macroporous products can also be prepared by incorporating soluble organic or inorganic compounds in the preparation. Soluble inorganic compounds, such as potassium chloride and sodium chloride, and soluble organic, such as sugar and maltose, are examples of useful materials for this preparation. Macroporous block composite materials (i.e. biphasic ceramics) can also be produced by mechanical manipulation using needle type tool to create the macroporous structure with pore size in a range of about 0.3 mm to about 1.5 mm.

EXAMPLES

Example 1

6 g of sintered HA (particle size smaller than 105 μm) was mixed with 8 g of $Ca(H_2PO_4)_2 \cdot H_2O$. This mixture was added with enough pure water to form paste. The paste was shaped to form a block and set at about 30 minutes to obtain a solid material. The solid material was leached with 50 ml of water each time. The leaching process was repeated until the surface pH of the solid material was about 5.5. The solid material was air dried to obtain a product in block form. X-ray study indicated that the product showed pure dicalcium phosphate dehydrate (DCPD) ceramic. Surface pH of the block product is near neutral. Further, part of the block product was crushed and passed a mesh to collect the granules with a size between 5 mesh and 35 mesh.

Pure DCPD ceramic in granular or block form was put in oven at temperature 100° C. or slighter higher for overnight to obtain pure dicalcium phosphate anhydrous (DCPA) ceramic.

Example 2

4 g of sintered HA (with particle size smaller than 150 μm) was mixed with 4.5 g of $Ca(H_2PO_4)_2$ and 3 g of sucrose. The mixture was added with enough water to form paste. The paste was kept in room temperature until it became a hardened solid material. The solid material was repeatedly leached with about 50 ml of pure water each time until the surface pH of the solid material was near 5.5. The final leached solid material was air dried to get a product with a nice macroporous structure. X-ray showed the product is pure DCPD ceramic. Part of pure DCPD ceramic was crushed and sieved to collect DCPD ceramic granules with a particle size between 0.5 mm to about 3 mm.

Example 3

2 g of sintered HA (with a particle size passed through 150 mesh) was mixed with 0.6 g $Ca(H_2PO_4)_2 \cdot H_2O$ and pasted with 0.7 g of pure water. The paste was shaped in a rectangular form and set at about 25 minutes to harden the paste to obtain a solid material. After setting, the hardened solid material was kept in air for several hours. After that, the solid material was leached and washed several times with pure water. The leaching and washing processes were repeated until the surface pH of the solid material was near 6 or slightly lower. The final leached solid material was air dried to obtain DCPD/HA biphasic ceramic with 2.8 g of weight and 2.52 g/cc of density.

The DCPD/HA biphasic ceramic was put in oven at temperature 100° C. or slighter higher for overnight to obtain DCPA/HA biphasic ceramic.

Example 4

2 g of sintered HA (with a particle size passed through 150 mesh) was mixed with 0.4 g $Ca(H_2PO_4)_2 \cdot H_2O$ and pasted with 0.6 g of pure water. The paste was shaped in a rectangular form and set at about 10 minutes to obtain a solid material. After setting, the hardened solid material was kept in air for several hours. After that, the solid material was leached and washed several time with pure water. The leaching and washing processes were repeated until the surface pH of the solid material was near 6 or slightly lower. The final leached solid material was air dried to obtain DCPD/HA biphasic ceramic with 2.3 g of weight and 2.54 g/cc of density.

While particular embodiments of the present invention have been shown and described, it will be obvious to those skilled in the art that, based upon the teachings herein, changes and modifications may be made without departing from this invention and its broader aspects. Therefore, the appended claims are intended to encompass within their scope of all such changes and modifications as are within the true spirit and scope of the exemplary embodiments of the present invention.

What is claimed is:

1. A method of manufacturing dicalcium phosphate dihydrate (DCPD) ceramic, dicalcium phosphate anhydrous (DCPA) ceramic, DCPD/hydroxyapatite (HA) biphasic ceramic, or DCPA/HA biphasic ceramic, comprising steps of:
    forming a mixture containing an acidic phosphate compound selected from the group consisting of monocalcium phosphate monohydrate, monocalcium phosphate anhydrous, phosphoric acid and a combination thereof, with a basic calcium phosphate compound comprising sintered HA;
    adding pure water without organic solvent or salts to the mixture so that the acidic phosphate compound reacts with the basic calcium phosphate compound to form paste of DCPD ceramic, DCPA ceramic, DCPD/HA biphasic ceramic or DCPA/HA biphasic ceramic;
    shaping the paste to a desired shape and hardening the paste to obtain a solid material;
    washing and leaching the solid material until a surface pH of the solid material reaches about 4.5 or higher; and
    drying the solid material at room temperature or below 95° C. to obtain DCPD ceramic or DCPD/HA biphasic ceramic, or drying the solid material at 100° C. or higher to obtain DCPA ceramic or DCPA/HA biphasic ceramic;
    wherein when the acidic phosphate compound is provided in an amount stoichiometrically equal to or in excess relative to the basic calcium phosphate compound, a reaction product is the DCPD ceramic or the DCPA ceramic; when the acidic phosphate compound is provided in the amount stoichiometrically less than the basic calcium phosphate compound, the reaction product is the DCPD/HA biphasic ceramic or the DCPA/HA biphasic ceramic.

2. The method of claim 1, further comprising a step of drying the solid material at room temperature to about 90° C. after the shaping and hardening step.

3. The method of claim 1, the basic calcium phosphate compound has a Ca/P molar ratio of more than 1, and the acidic phosphate compound has a Ca/P molar ratio of less than 1.

4. The method of claim 1, wherein the acidic phosphate compound is provided in the amount stoichiometrically in excess of about 0.1% to about 20% by weight of the basic calcium phosphate compound for obtaining the DCPD ceramic or the DCPA ceramic.

5. The method of claim 4, wherein the DCPD ceramic or the DCPA ceramic is at least 97% in purity.

6. The method of claim 1, wherein HA used is fine powder or in granular form with a particle size in a range of about 0.1 mm to about 2 mm.

7. The method of claim 1, wherein the DCPD ceramic, DCPA ceramic, DCPD/HA biphasic ceramic, or DCPA/HA biphasic ceramic is in granular form or in block form.

8. The method of claim 7, wherein the DCPD ceramic, DCPA ceramic, DCPD/HA biphasic ceramic, or DCPA/HA biphasic ceramic is in granular form with a particle size in a range of about 0.1 mm to about 5 mm.

9. The method of claim 7, wherein the DCPD ceramic, DCPA ceramic, DCPD/HA biphasic ceramic, or DCPA/HA biphasic ceramic is in block form with a porous structure.

10. The method of claim 1, wherein the DCPD/HA biphasic ceramic or DCPA/HA biphasic ceramic comprises dicalcium phosphate minerals from about 30% to about 95% by weight and HA from about 5% to about 70% by weight.

11. The method of claim 1, wherein the mixture further comprises porogen.

12. The method of claim 11, wherein the porogen comprises sodium chloride, potassium chloride, maltose, sucrose, or a combination thereof.

* * * * *